(12) United States Patent
Klingenbeck-Regn

(10) Patent No.: US 7,376,214 B2
(45) Date of Patent: May 20, 2008

(54) METHOD AND APPARATUS TO IMAGE AN ORGAN

(75) Inventor: Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 107 days.

(21) Appl. No.: 10/911,796

(22) Filed: Aug. 5, 2004

(65) Prior Publication Data

US 2005/0058248 A1 Mar. 17, 2005

(30) Foreign Application Priority Data

Aug. 7, 2003 (DE) ................. 103 36 278

(51) Int. Cl.
*A61B 6/03* (2006.01)
*H05G 1/60* (2006.01)

(52) U.S. Cl. .................. 378/8; 378/95; 600/428

(58) Field of Classification Search ............ 378/8, 378/15, 95, 196–198; 600/428
See application file for complete search history.

(56) References Cited

U.S. PATENT DOCUMENTS

| | | | | |
|---|---|---|---|---|
| 5,262,946 A * | 11/1993 | Heuscher | ............ | 378/15 |
| 5,832,051 A * | 11/1998 | Lutz | ............ | 378/8 |
| 6,085,754 A * | 7/2000 | Alferness et al. | ............ | 128/898 |
| 6,233,308 B1 * | 5/2001 | Hsieh | ............ | 378/62 |
| 6,233,478 B1 * | 5/2001 | Liu | ............ | 600/428 |
| 6,269,140 B1 * | 7/2001 | Takagi et al. | ............ | 378/8 |
| 6,324,254 B1 | 11/2001 | Pflaum | ............ | 378/95 |
| 6,353,653 B1 * | 3/2002 | Edic | ............ | 378/8 |
| 6,370,217 B1 | 4/2002 | Hu et al. | ............ | 378/8 |
| 6,373,920 B1 * | 4/2002 | Hsieh | ............ | 378/98.11 |
| 6,426,990 B1 * | 7/2002 | Cesmeli | ............ | 378/8 |
| 6,466,638 B1 * | 10/2002 | Silver et al. | ............ | 378/4 |
| 6,470,066 B2 * | 10/2002 | Takagi et al. | ............ | 378/8 |
| 6,504,894 B2 * | 1/2003 | Pan et al. | ............ | 378/8 |
| 6,628,742 B2 * | 9/2003 | Pan et al. | ............ | 378/8 |
| 6,628,981 B2 * | 9/2003 | Baker et al. | ............ | 600/425 |
| 6,697,451 B2 * | 2/2004 | Acharya et al. | ............ | 378/18 |
| 6,718,004 B2 * | 4/2004 | Cesmeli | ............ | 378/8 |
| 6,865,248 B1 * | 3/2005 | Rasche et al. | ............ | 378/8 |
| 7,027,855 B2 * | 4/2006 | Okerlund et al. | ............ | 600/509 |

\* cited by examiner

*Primary Examiner*—Allen C. Ho
(74) *Attorney, Agent, or Firm*—Schiff Hardin LLP

(57) ABSTRACT

A method is provided to image an organ of the human or animal body using and acquisition device rotating over an angle, in that the rotation speed of the rotating acquisition device is modulated dependent on a reference signal that represents a current movement state of the organ to be imaged. Additionally or alternatively, the measurement interval in which the acquisition of the organ ensures during the rotation can respectively be adapted using the reference signal to a cycle duration of the movement of the organ to be imaged. Moreover, a corresponding apparatus to implement such a method is provided.

18 Claims, 4 Drawing Sheets

METHOD AND APPARATUS TO IMAGE AN ORGAN

BACKGROUND OF THE INVENTION

The invention concerns a method and an apparatus to image an organ of the human or animal body, particularly for imaging a beating heart via a rotating acquisition device.

In modem medicine, manifold minimally-invasive methods to image an organ are known, such as x-ray methods. It is the goal of these methods to obtain a comprehensive knowledge of the respective organ and its state primarily without opening the body. In a known application, for example, a C-arm of an x-ray apparatus with an x-ray tube and an x-ray detector is rotated around a patent, normally around the patient longitudinal axis, with a constant rotation speed or angular velocity w over an angle of, for example, 300 degrees. Instead of an only platform view through a catheter with camera, etc., with such imaging methods and a corresponding apparatus, a number of individual exposures of the appertaining organs can be acquired from various spatial directions, on whose basis three-dimensional images or other representations (such as, in particular, arbitrary cross-sections) can ultimately be produced. With these methods, for example, the heart muscle and the coronary artery can be examined without a catheter.

However, for a 3D reconstruction, only those images can be used that show the organ in a respectively constant state. In a preferred and most important application case, the exposure of the heart, the filling phase or diastole, as a relative rest phase of the heart, is selected as a representation state. In a living human and in a rest position given relaxation, this rest phase lasts less than 200 milliseconds. During the acquisition, however, only a few projections for the 3D reconstruction and modeling can be collected by the moving acquisition device in a time window $\Delta t$ in the rest phase of the heart cited above.

The respective data collected outside of the acquisition time window $\Delta t$ cannot be used for imaging due to the heart movement. These data losses lead to large gaps in the space of the projection angle $\alpha$, and therewith to an incomplete representation basis of the entire organ. At best, interpolations with relatively uncertain assumptions can be effected within these representation gaps. A similar problem also occurs with other organs whose shape and/or positions change over time. However, for reasons of keeping low a total radiation exposure with an x-ray tube continuously located in operation, the acquisition device may not exhibit an arbitrarily slow rotation speed in order to acquire optimally many exposures from different spatial directions at advantageous acquisition moments. For the same reasons, a measurement can also not be repeated arbitrarily often.

For this reason, U.S. Pat. No. 6,324,254 discloses the acquisition of a rhythmically moving vessel to in fact move the C-arm with an optimally slow rotation speed, preferably >2° per second to thereby implement individual image acquisitions triggered by the vessel movement or an organ movement causing the movement of the vessel. This means radiation is only respectively emitted by the x-ray tube and an exposure made at specific times while the C-arm moves around the patent with an optimally slow, constant speed.

The constant rotation speed is hereby preferably established before the measurement dependent on the frequency of the rhythmic vessel or organ movement in order to ensure that a minimum number of exposures can be generated during a measurement. However, this procedure has the disadvantage that the measurement lasts a relatively long time. In this time, the patent must lie absolutely still. Even minimal position changes can lead to impaired measurement.

A similar method is disclosed in U.S. Pat. No. 6,370,217 for measuring a periodically moving subject with a computer tomograph. Given a measurement with such a computer tomography system, the x-ray tube rotates multiple times around the patient with a very high speed, for example, with a speed in the range of approximately 1 s/rotation. In order to thereby always acquire the cyclically changing subject in the same state, here as well when the x-ray tube momentarily emits x-ray radiation, the imaging is controlled to be triggered by the movement cycle in order to thus make individual exposures.

Likewise, a constant rotation speed is hereby preferably determined before the measurement dependent on the frequency of the rhythmic vessel or organ movement. The rotation speed is thereby adjusted such that exposures are optimally generated from all spatial directions during a measurement This method Is, however, not usable for a measurement with a C-arm or similar acquisition device, since in such a relatively simple acquisition device, the x-ray tube and the detector can not be moved arbitrarily fast and often around the patient (this is different than in a significantly more elaborately constructed computer tomography apparatus). Typically, only a rotation angle of maximally 300° is available.

SUMMARY OF THE INVENTION

It is therefore an object of the present invention to provide a method and an apparatus to the effect that a ratio of angle gaps to usable angular intervals is provided in order to increase the reliability and precision of the entire measurement.

This object is inventively achieved via a method of the previously cited type in which the rotation speed of the rotating acquisition device is modulated dependent on a reference signal that represents a current movement state of the organ to be imaged.

Via the appropriate modulation of the rotation speed, the rotation movement can be adapted to the changes of the position and/or shape of the organ to be acquired, and thus the acquisition can be optimized. The modulation thereby advantageously ensues such that the ratio of useable angular intervals to angle gaps is increased. The angular coverage is optimally dense with "valid" (meaning usable) image data around the examined body.

An apparatus to implement this acquisition method comprises an acquisition device that is positioned such that it can rotate around the body by at least one angle and an appropriate actuator in order to pan the acquisition device with a predetermined rotation speed around the body during a measurement Moreover, this apparatus comprises a measurement device to determine a suitable reference signal which represents a current movement state of the organ to be imaged and a control device connected with the actuation unit which correspondingly modulates the rotation speed of the rotating acquisition device dependent on the reference signal.

Various embodiments of the method and apparatus are discussed below.

Various embodiments of the method can particularly be used on the previously cited C-arm acquisition devices, which comprise a C-arm suspended such that it can be rotated around the body, having at one C-end an x-ray source and at the other end an x-ray detector opposite the x-ray source. However, in principle the method can also be used with other similar acquisition devices.

This method is particularly well-suited when the movement of the organ to be acquired moves periodically, such as the heart rhythm in heart exposures. Given a periodic movement of the organ, the modulation of the rotation speed likewise preferably ensues periodically. A "modulation of the rotation speed" is also defined as including every other movement, for example, also a periodic deviation from a constant movement.

In the theoretically simplest case, the rotation could be entirely stopped at specific points in time, for example, between the rest phases of the organ. Due to the weight or moment of inertia of the acquisition device, however, in most cases this can only technically be realized with great effort. Therefore, the modulation preferably ensues such that the acquisition device alternately rotates faster and slower. The faster rotation with a first angular velocity occurs during the measurement or exposure intervals $\Delta t$. The slower rotation occurs with a second angular velocity between two successive measurement intervals.

Depending on a specific application case, different signals can be drawn upon as reference signals. In the preferred case of monitoring and imaging a heart and/or one of its vessels, an EKG signal of the patient is preferably evaluated. Alternatively or additionally, the pulse of the patient and/or ultrasound signals, etc. can also be used.

It is particularly advantageous when the measurement interval with the useable exposures of the organ is adapted to the cycle duration of a periodic movement of the organ to be imaged, for example, given a heart acquisition adapted to the heart period length $T_{rr}$. The cycle duration can, for example, preferably also be determined in a sliding/floating manner beforehand over a certain number of movement cycles. The length of the measurement interval can, for example, be specified in percentages of the cycle duration. If, using the reference signal, it is established that the cycle duration changes during the acquisition, a synchronous adaptation of the measurement interval can ensue.

Such an adaptation (by way of a reference signal) of the measurement interval to the cycle duration of a movement of the organ to be imaged is also advantageously independent of the modulation of the rotation speed of the acquisition device in order to increase the ratio of usable angular intervals to angular gaps, and can therefore also be viewed as an independent embodiment of the present invention.

Further advantageous embodiments are discussed below.

The transition region between the phases of different rotation speeds are preferably designed with different acceleration curves or braking curves dependent on the capability of the electromechanical control. These transitions are designed continuous and preferably sinusoidal according to an embodiment of the invention.

Naturally, differently designed transition curves can also be used. For example, in one embodiment, under a requirement of a temporal interval, the transition curves are formed with the aid of energy-optimized functions, for example, using cubic splines. Provided with the respective boundary values, the regulation parameters are determined by a computer in real time. $T_{rr}$, $\Delta t$, $\omega_1$ and $\omega_2$ and possible further quantities are determined by the computer according to one or more of the above specifications. These quantities are subsequently transferred to a control unit of the acquisition device as regulation specifications.

A deactivation of x-ray radiation, or at least a reduction of the emitted radiation to an optimally low intensity or dose is advantageously provided outside of the measurement intervals. An effective reduction of the total radiation exposure for the patient is also achieved with only one pass of the apparatus according to an embodiment of the inventive method.

In a further embodiment of the invention, the user may retrospectively displace the measurement intervals on the time axis in a later evaluation of the acquired data in order to compensate for stronger oscillations of the heart rate or arrhythmias. This measure is inasmuch reasonable since normally all image data determined during the measurement in a pass is cached anyways, such that they are in every case available for a post-processing. If necessary, even such data that were acquired outside of the actual predetermined "valid" measurement intervals $\Delta t$ are thus present for post-processing. In this case, an automatic adaptation of the appertaining angular intervals $\Delta \alpha$ ensues according to the known control curves.

The inventive control device or its components can preferably largely be realized in the form of software in a processor or a conventional computer-aided control of the acquisition device. In this manner, it is possible to also upgrade the method described above in the form of a computer program product, particularly an update in existing apparatuses.

DESCRIPTION OF THE DRAWINGS

The invention is explained in detail in the following using an exemplary embodiment, with reference to attached Figures.

DETAILED DESCRIPTION OF THE PREFERRED EMBODIMENTS

Figure 1:
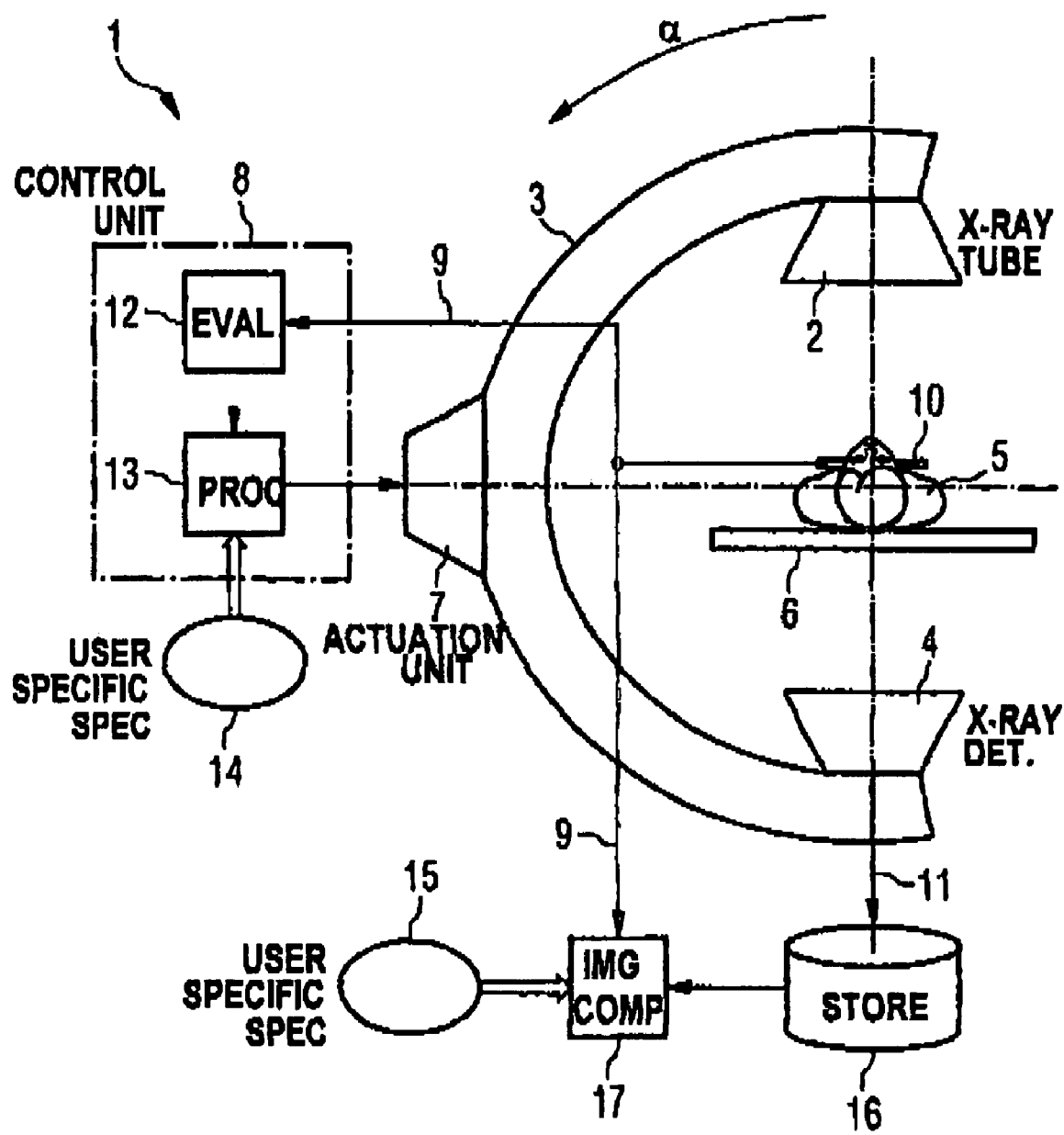
FIG. 1 is a schematic block diagram representation of an exemplary embodiment of an inventive imaging apparatus.

In a schematic representation, FIG. 1 shows an imaging examination apparatus 1 in which an x-ray tube 2 is rotated on a "C-arm" 3, together with a surface detector 4 arranged oppositely on the C-arm 3, at an angle $\alpha$ around the body 5 of a patient to be examined. The patient is positioned on a patient positioning table 6. The rotation of the C-arm 3 ensues around the longitudinal body axis of the patient The surface detector 4 can, for example, be an image intensifier or a planar detector (FPD).

During a movement $\alpha(t)$ of the C-arm 3 around the body 5 of the patient to be examined, x-ray exposures are acquired from different spatial directions. With this examination lasting only 10 to 15 s, internal organs of the patient can be reproduced as a three-dimensional model. As the most important application case, an embodiment of exclusively a heart examination is discussed in the following, without limitation of the use of the inventive method and/or the use of the inventive apparatus.

Rotation of the C-arm 3 is provided with a motorized actuation unit 7. This is controlled by a control unit 8 under evaluation and preparation of a reference signal 9 that reproduces the movement state of the heart to be acquired here. The reference signal 9 is determined by a measurement device 10, here a typical EKG detector.

The detailed design of the apparatus 1 and its components is discussed below following a representation of a principle course of the method for 3D modeling and particular problems.

If the x-ray tube 2 and the surface detector 4 are moved on the C-arm 3 with a constant rotation speed or angular velocity ω around the body 5 of the patient, only a few projections can be collected for a 3D reconstruction in a time window Δt in the rest phase of the heart the filling phase or diastole. The images acquired outside of the time window Δt and other data 11 can not be used for imaging due to the heart movement This principle selection leads to large gaps in the space of the projection angle α.

This becomes apparent in a concrete numerical example:

Given the typical constant angular velocity w according to the prior art, the connection between projection angle α(t) and time t is given by the function:

$$\alpha(t)=\alpha_0+\omega \cdot t,$$

where $\alpha_0$ is the initial value at a point in time t=0.

Figure 2:
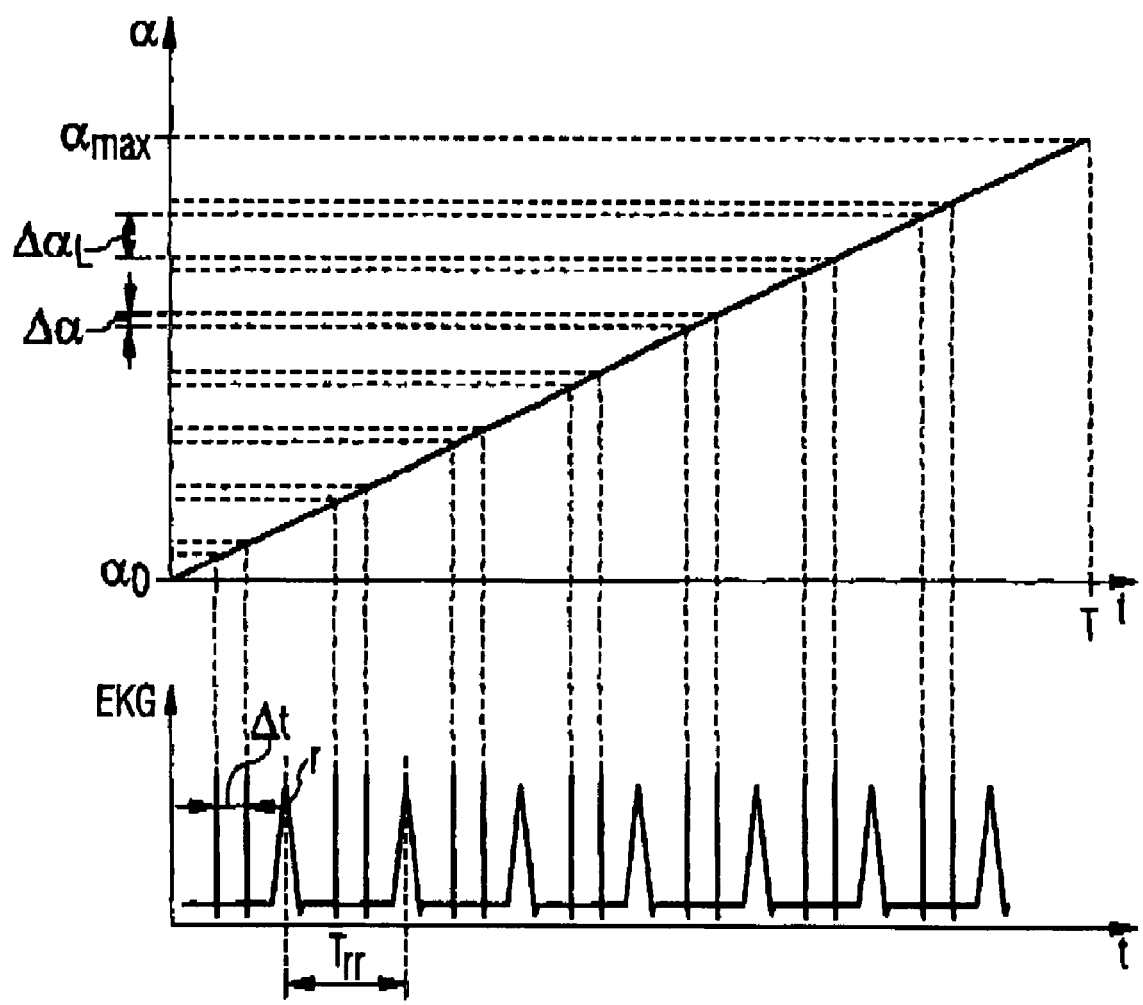
FIG. 2 is a graph illustrating a curve of the angle dependent on the time given constant angular velocity according to the prior art.

This connection and the relation of the heart movement (represented by a reference signal taken from the patent in the form of an EKG signal 9) are shown in FIG. 2.

An angular velocity ω=30 degrees/s results for an overall rotation angle of $\alpha_{max}$=300 degrees and a total rotation or acquisition time of T=10. Given a time resolution typically necessary for the heart imaging, the usable measurement interval for the acquisitions lies in the range of Δt<200 ms. An angular interval Δα of usable projections of $$\Delta\alpha=\omega \cdot \Delta t=30 \text{ degrees/s} \cdot 0.2 \text{ s}=6$$

thereby results.

Given a heart rate $1/T_{rr}$ of 60 bpm (heartbeats per minute), the length $T_{rr}$ of a heartbeat period, which is here defined as a time between successive r-spikes of an EKG, is here precisely one second, thus $T_{rr}$=1 s. This means that the C-arm 3 rotates further for a time of $T_{rr}-\Delta t$=0.8 s, and data are acquired that are in principle not usable for the imaging due to the pumping motion of the heart In the space of the projection angle, this means a gap $\Delta\alpha_L$ of $$\Delta\alpha_L=0.8 \text{ s} \cdot 30 \text{ degrees/s}=24 \text{ degrees}$$

The ratio R of the usable angular intervals Δα to the angular gaps $\Delta\alpha_L$ is consequently very unfavorable. In the present example, R is:

$$R = \frac{\Delta\alpha}{\Delta\alpha_L} = 25\%$$

In other words, only a fourth of the available spatial directions in the scan plane is used to achieve an optimally reliable basis for a modeling of the heart to be imaged.

For an ideal acquisition of usable data, the angular gaps should be virtually non-existent. The ratio R would therewith be arbitrarily large. As long as the C-arm 3 is rotated with constant angular velocity, however, the ratio R is independent of the rotation speed.

The rotation speed is therefore modulated during the rotation around the patient such that R is increased. The angular coverage is therewith optimally dense with "valid" or usable data.

Figure 3:
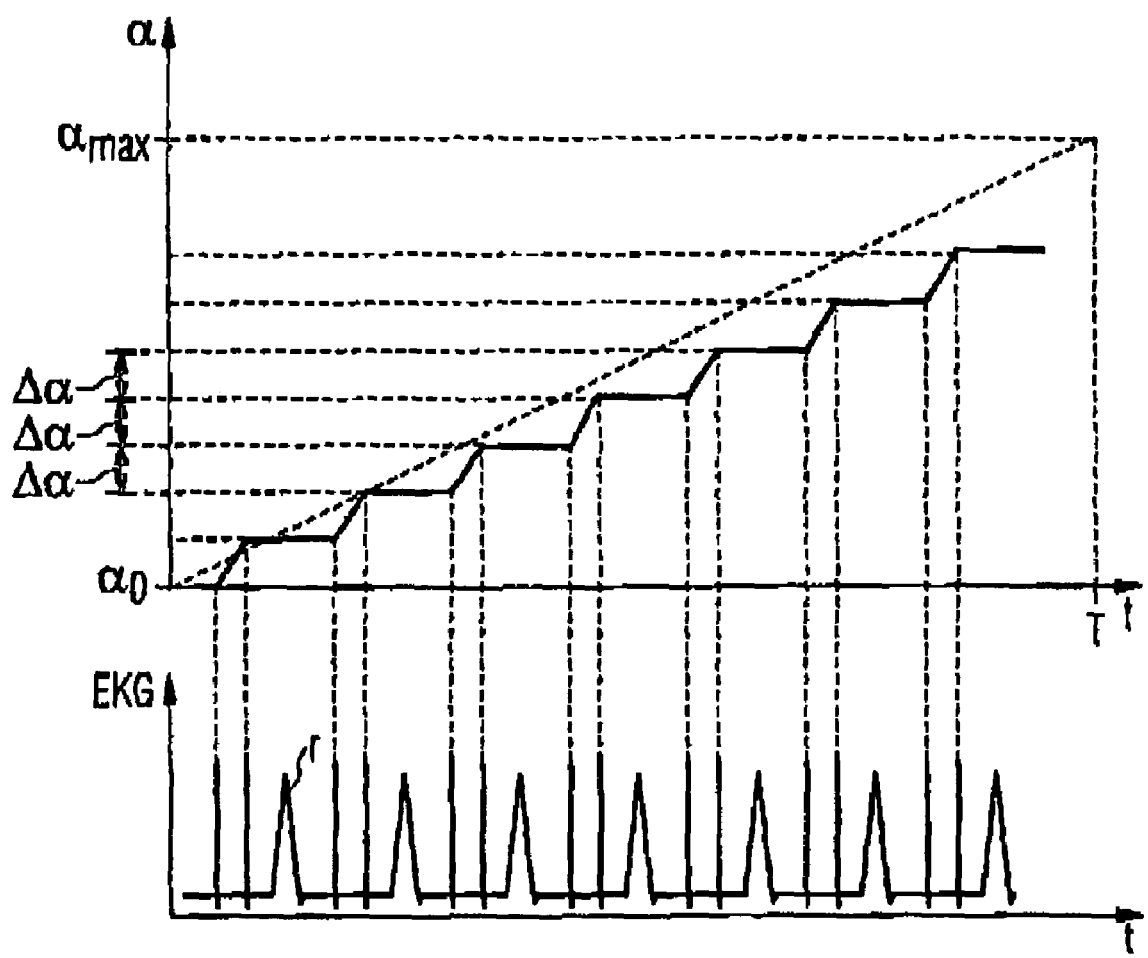
FIG. 3 is a graph illustrating an ideal angle-time curve.

An ideal case would then be achieved when the rotation between two measurement intervals Δt is interrupted into successive heartbeats. The curve of the projection angle as a function of time shown in FIG. 3 results. Since $\alpha_L$ is zero, R is infinitely large, and therewith the angular coverage with "valid" data is absolute.

However, the arrangement that can be moved over the C-arm 3 comprises a non-negligible mass. For reasonable delimitation of the technical or electromechanical effort for the actuation unit 7 of the C-arm 3, for a practical realization, it is significantly more appropriate to not completely interrupt the rotation. Rather, for the movement, a modulation between an alternately faster and slower rotation is selected. The rotation thereby ensues faster with a first angular velocity $\omega_1$ during the measurement intervals Δt and slower between two successive measurement intervals with a second angular velocity $\omega_2$.

Figure 4:
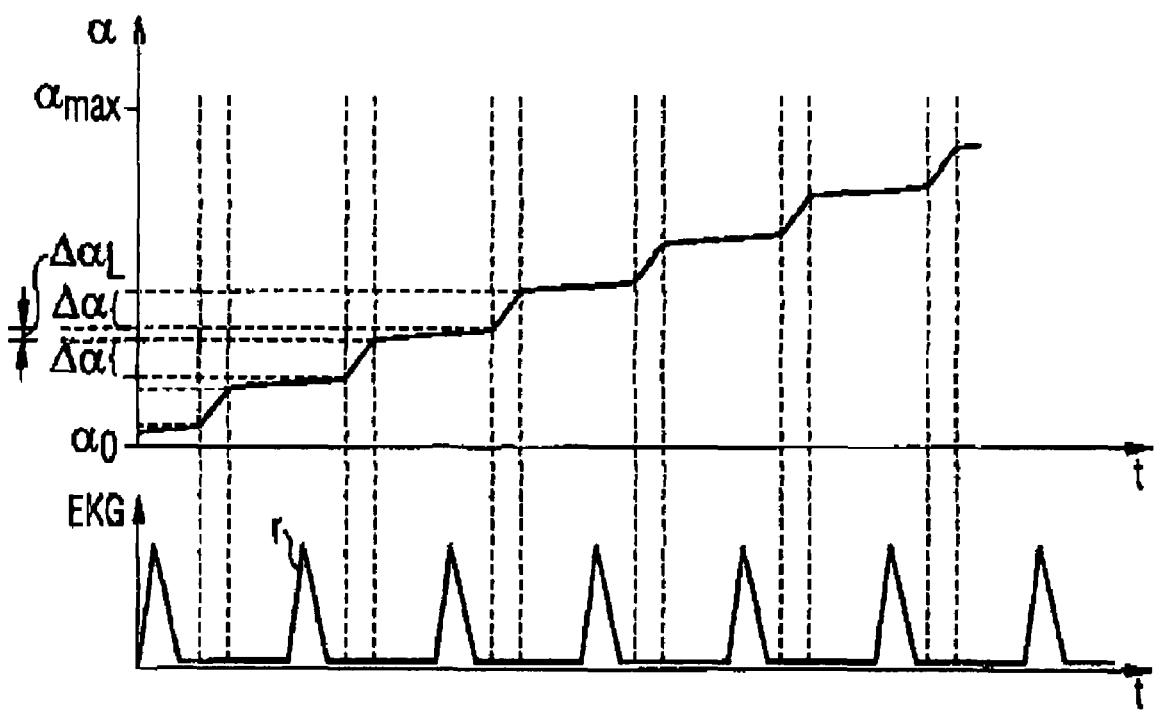
FIG. 4 is a graph illustrating a real angle-time curve.
Figure 5:
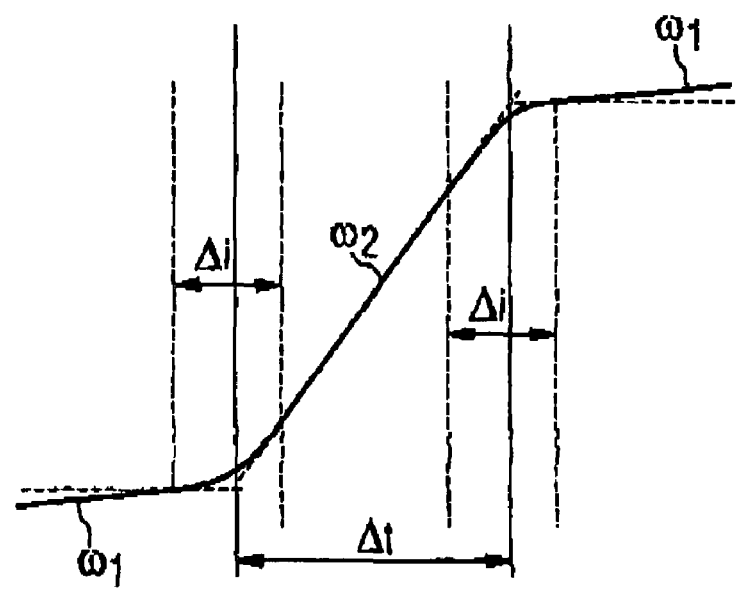
FIG. 5 is a graph showing a detail enlargement of a section of the diagram according to FIG. 4.

The transition range can be designed with various acceleration curves or braking curves depending on the capacity of the electromechanical control and the actuation unit 7. A possible angle-time diagram is shown in FIG. 4. FIG. 5 shows an enlarged section of FIG. 4. The dashed curves represent the ideal curve according to FIG. 3; the solid lines represent a curve according to FIG. 4 that can be realized relatively simply.

It is then true for the angle ratio:

$$\Delta\alpha = \omega_1 \cdot \Delta t$$

$$\Delta\alpha_L = \omega_2 \cdot (T_{RR} - \Delta t)$$

$$R = \frac{\omega_1 \cdot \Delta t}{\omega_2 \cdot (T_{RR} - \Delta t)} = \frac{\omega_1}{\omega_2} \cdot \frac{1}{\left(\frac{T_{RR}}{\Delta t} - 1\right)}$$

In the following two limit cases, R is infinitely large:

a) $\omega_2$=0, i.e., given a theoretical limit case of a completely stopped rotation outside of the measurement intervals Δt.

b) $\Delta t = T_{rr}$, i.e., all measurement values are considered independent of the movement state of the heart, since measurements are made over the whole period length of a heart cycle. In this case, undiminished movement artifacts are correspondingly obtained in the images.

The modulation should ensue dependent on the heart rate $1/T_{rr}$ and measurement or exposure interval length Δt, such that the ratio size R is maximal in the scope of the electromechanical control possibilities of the C-arm 3.

For this, a further example is illustrated in the following:

A pulse of 60 min$^{-1}$ corresponds to the heart rate $1/T_{rr}$=60 bpm. The length of a heart period $T_{rr}$=1 s results from this. $\omega_1$=3·ω and $\omega_2$=ω/3 are also selected given a measurement interval Δt=200 ms. In this case, it is true that:

$$R = \frac{3\omega}{\omega/3} \cdot \frac{200}{800} = 9 \cdot \frac{1}{4} = 2.25$$

The ratio R can thus be increased by a factor of 9 relative to the unmodulated case of the preceding example.

With ω=30 degrees/s, $$\Delta\alpha=90 \text{ degrees/s} \cdot 0.2 \text{ s}=18 \text{ degrees}$$

$$\Delta\alpha_L=10 \text{ degrees/s} \cdot 0.2 \text{ s}=6 \text{ degrees}$$

result for the angular ranges. The usable angular ranges Δα are thus significantly increased; the angular gaps $\Delta\alpha_L$ are thus clearly reduced.

Given this modulation, the average angular velocity is 26 degrees/s. The total acquisition time for a rotation over 300 degrees is approximately 12 s. Compared with the acquisition time of 10 s given a rotation of the C-arm 3 with a constant angular velocity, this is, in totally, only insignificantly longer.

The transitions between the regions of different angular velocities $\omega_1$, $\omega_2$ are designed under consideration of the respective electromechanical possibilities of the apparatus 1. Braking and acceleration in the rapid changeover represent severe stresses for the apparatus 1. A great deal of electrical energy is absorbed by the actuation unit 7 and re-emitted in the form of heat.

In a transition between the different angular velocities $\omega_1$, $\omega_2$, an interval of $\Delta i$ is therefore advantageously selected in which the angular velocity is adjusted from an old desired value to a new desired value. Here, under consideration of the current limit parameters, an energy-optimized curve shape is selected as a desired curve. A cubic spline function has been selected, as reproduced as a section enlargement in FIG. 5. Alternatively, a sinusoidal transition curve could also be selected. A possible mechanical oscillation of the overall system effected by the rapid changeover of braking and acceleration can be prevented via countermeasures known to one of ordinary skill in the art.

The method specified in the preceding is implemented based on an EKG signal as a reference signal 9. The apparatus 1 is permanently monitored and controlled by the control unit 8 during the running acquisition. For this, within the control unit 8, an evaluation unit 12 exists to evaluate the EKG signal 9 that is supplied by the measurement device 10. The evaluation unit 12 feeds an internal processor unit 13. The control signals for the actuation unit 7 of the C-arm 3 and for the x-ray source 2 or its control and the detector 4 are generated in the processor unit 13, possibly under user-specific requirements 14. A deactivation of the x-ray radiation or a reduction to an optimally low dose or intensity can thereby ensue within the time sections $T_{rr}-\Delta t$ not used for the measurement, i.e., outside of the measurement intervals $\Delta t$.

To improve the measurement results, an average value of the parameters can also be determined from the EKG signal 9, for example, in the course of a preliminary measurement in the evaluation unit 12, this average value being necessary for the regulation of a movement of the C-arm 3 to be planned. Primarily, these are the heart rate $1/T_{rr}$ and the time window $\Delta t$ of the diastole. These average values can also be continuously updated over a specific interval during the measurement such that each change is immediately taken into account in the regulation.

The raw image data 11 acquired during and also after the measurement are stored in a storage area 16. These raw data 11 can undergo any known form of post-processing for image material in a typical image computer 17. It is therewith possible to also subsequently displace the measurement intervals retrospectively on the time axis in order compensate for stronger oscillations of the heart rate $1/T_{rr}$ or arrhythmias.

Arrhythmias change the respective acquisition intervals at. An acquisition interval $\Delta t$ in a rest phase of the heart is normally shortened by an irregularity in the form of an arrhythmia, at least in the appertaining heart cycle. Such effects are identified using an examination of the likewise acquired reference signal 9 implemented after the conclusion of the actual acquisition time T. A correction of the data then possibly ensues again under user-specific requirements 15, for example via a masking of the image data that were determined within the phase of an irregularity. In spite of the loss of image information, an overall improved 3D model can therewith be reconstructed since the prepared data are more reliable.

In the case of arrhythmias or strong oscillations of the heart rate $1/T_{rr}$, an automatic adaptation of the angular intervals $\Delta\alpha$ affected by irregularities also ensues during the measurement, possibly with inclusion of further user-specific specifications 14. It is thereby taken into account that known irregularities periodically reoccur at specific intervals and/or contain preceding or subsequent signal portions that likewise invalidate image information.

These embodiments of the invention open the possibility to significantly Improve the imaging of a beating heart with a rotating C-arm with very simple and cost-effective mechanisms. For the rest, it offers to refit existing x-ray systems, which already comprise an motorized x-ray source 2 that can be moved into arbitrary positions, and a corresponding x-ray detector 4, with a control device and a suitable detector control device in order to also use these systems according to the inventive method. Insofar as these systems already comprise control devices with suitable processors, an update of the control software with suitable control software modules is possibly also sufficient.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the Various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

REFERENCE LIST 1 examination apparatus
2 x-ray tube
3 acquisition device/C-arm
4 x-ray detector
5 body
6 patient positioning table
7 actuation unit
8 control unit
9 reference signal/EKG signal
10 measurement device
11 raw image data
12 evaluation unit
13 processing unit
14 user-specific specifications
15 user-specific specifications
16 storage
17 image computer
α angle
$α_0$ start angle at t=0
$α_{max}$ maximum adjustable angle
Δα a angular range with usable exposures
$Δα_L$ angular range with unusable exposures
Δi interval for increase compensation
R ratio size
ω angular velocity
Δt measurement interval
t time
T total acquisition time
$T_{rr}$ heart period length

What is claimed is:

1. A method for imaging an organ exhibiting movement that causes said organ to change position or change shape, of a living subject, comprising the steps of:
   irradiating the organ with an x-ray beam by rotating the x-ray beam in a rotation extending only through an angle that is less than 360°, and acquiring attenuation data, resulting from the irradiation of the organ with said x-ray beam, only during actual, non-zero movement of the x-ray beam in said rotation;
   acquiring a signal representing movement of the organ during said rotation of said x-ray beam;
   modulating a rotation speed of the actual, non-zero movement of said x-ray beam dependent on said signal by adapting said rotation speed to at least one of said change in position or change in shape of said organ, making said rotation speed non-constant within said angle; and
   generating a complete image of the organ from said attenuation data.

2. A method as claimed in claim 1 wherein the step of irradiating the organ with an x-ray beam comprises generating said x-ray beam with an x-ray source mounted on a C-arm and rotating said C-arm around the living subject, and wherein the step of acquiring attenuation data comprises detecting said x-ray beam with an x-ray detector also mounted on said C-arm and rotated around the living subject.

3. A method as claimed in claim 1 wherein the step of modulating said rotation speed also comprises momentarily halting or delaying rotation of said x-ray beam within specific temporal intervals.

4. A method as claimed in claim 1 wherein the step of modulating said rotation speed comprises alternatingly slowing and increasing said rotation speed.

5. A method as claimed in claim 1 wherein the step of modulating said rotation speed comprises increasing said rotation speed at an angular velocity during a data acquisition interval.

6. A method as claimed in claim 5 wherein said angular velocity is a first angular velocity, and wherein the step of modulating said rotation speed comprises slowing said rotation speed with a second angular velocity, different from said first angular velocity, between successive data acquisition intervals.

7. A method as claimed in claim 1 wherein the organ is a heart, and wherein the step of acquiring said signal representing said movement of said organ comprises acquiring a signal representing a heart beat of the heart.

8. A method as claimed in claim 7 comprising acquiring an ECG signal as said signal representing beating of the heart.

9. A method as claimed in claim 1 wherein the movement of the organ occurs in cycles each having a cycle duration, and comprising the step of adapting a data acquisition interval, within said angle, to said cycle duration averaged over a plurality of said cycles.

10. A method as claimed in claim 1 wherein the step of modulating said rotation speed comprising:
   rotating said x-ray beam respectively in two portions of said angle at different rotation speeds, with a transition range between said two portions; and
   in said transition range, adapting said rotation speed between said different rotation speeds by rotating said x-ray beam according to a predetermined curve selected from the group consisting of an acceleration curve and a deceleration curve.

11. A method as claimed in claim 1 comprising acquiring said attenuation data within a measurement interval in said angle, and deactivating or reducing an intensity of said x-ray beam outside of said measurement interval.

12. A method as claimed in claim 1 comprising acquiring said attenuation data in successive measurement intervals and electronically post-processing said acquisition data, to form said image, with said measurement intervals being respectively displaced with respect to a time axis to compensate for said movement of the organ.

13. An x-ray imaging apparatus for imaging an organ exhibiting movement that causes said organ to change position or change shape comprising:
   an x-ray source that emits an x-ray beam;
   an x-ray detector;
   a rotatable mount to which said x-ray source and said x-ray detector are mounted, said rotatable mount being rotatable around a subject containing the organ, to irradiate the organ with said x-ray beam by rotation only through an angle that is less than 360°, with said x-ray detector detecting attenuation data representing said x-ray beam attenuated by the organ only during actual, non-zero rotational movement of said x-ray beam within said rotation;
   a measurement device configured to interact with the subject to obtain a signal representing the movement of the organ during said rotation of said x-ray beam;

a control unit connected to said rotatable mount that modulates a rotation speed of the actual, non-zero rotational movement of said rotatable mount dependent on said signal, by adapting said rotation speed to at least one of said change in position or change in shape of said organ, making said rotation speed of the actual, non-zero rotational movement non-constant within said; and a computer that reconstructs a complete image of the organ from said attenuation data.

14. An apparatus as claimed in claim 13 wherein said rotatable mount is a C-arm having opposite ends, with said x-ray source and said x-ray detector being respectively mounted at said opposite ends.

15. An apparatus as claimed in claim 13 wherein said control unit comprises an evaluation unit that electronically pre-processes said signal.

16. An apparatus as claimed in claim 13 wherein said x-ray detector acquires said attenuation data in a measurement interval within said angle, and comprising an x-ray source control unit that deactivates or reduces an intensity of said x-ray beam outside of said measurement interval.

17. An apparatus as claimed in claim 13 wherein said organ is a heart, and wherein said measurement device acquires an EGG as said signal.

18. A storage medium encoded with computer-readable data, said storage medium being loadable into a control unit of an imaging apparatus that controls rotation of an x-ray beam around a subject, containing an organ exhibiting movement, to cause the subject to be irradiated with the x-ray beam, with attenuation data from the organ being detected and electronically combined to form a complete image of the organ, said data programming said control unit to modulate a rotation speed of the x-ray beam during actual, non-zero rotational movement of the x-ray beam only through an angle that is less than 360° while irradiating the organ, so that said rotation speed of the actual, non-zero rotational movement of the x-ray beam within said angle is non-constant.

* * * * *